United States Patent [19]

Collins et al.

[11] Patent Number: 5,105,810

[45] Date of Patent: Apr. 21, 1992

[54] IMPLANTABLE AUTOMATIC AND HAEMODYNAMICALLY RESPONSIVE CARDIOVERTING/DEFIBRILLATING PACEMAKER WITH MEANS FOR MINIMIZING BRADYCARDIA SUPPORT PACING VOLTAGES

[75] Inventors: Kenneth A. Collins, Neutral Bay; Philip J. Maker, Sydney, both of Australia

[73] Assignee: Telectronics Pacing Systems, Inc., Englewood, Colo.

[21] Appl. No.: 557,248

[22] Filed: Jul. 24, 1990

[51] Int. Cl.$^5$ .............................................. A61N 1/365
[52] U.S. Cl. ......................... 128/419 D; 128/419 PG
[58] Field of Search ...... 128/419 PT, 419 D, 419 PG

[56] References Cited

U.S. PATENT DOCUMENTS

| | | | |
|---|---|---|---|
| 3,614,955 | 10/1971 | Mirowski et al. | 128/419 D |
| 3,942,536 | 3/1976 | Mirowski et al. | 128/419 D |
| 4,114,627 | 9/1978 | Lewyn et al. | 128/419 PT |
| 4,114,628 | 9/1978 | Rizk | 128/419 PT |
| 4,280,502 | 7/1981 | Baker, Jr. et al. | 128/419 PG |
| 4,702,253 | 10/1987 | Nappholz et al. | 128/419 PG |
| 4,774,950 | 10/1988 | Cohen | 128/419 D |
| 4,817,605 | 4/1989 | Sholder | 128/419 PT |
| 4,869,252 | 9/1989 | Gilli | 128/419 PG |
| 4,895,151 | 1/1990 | Grevis et al. | 128/419 D |

OTHER PUBLICATIONS

Cohen, T. J. et al., "Hemodynamic Responses to Rapid Pacing: A Model for Tachycardia Differentiation," *Pace*, vol. 11, pp. 1522-1528, Nov. 1988, Part I.
Williams et al., "Automatic Implantable Cardioverter-Defibrillator-Related Complications," J.A.C.C., vol. 15(2), p. 55A (1990).
D. Williams et al., "Automatic Implantable Cardioverter-Defibrillator Related Complications," J.A.C.C., vol. 15(2), p. 55A (1990).

*Primary Examiner*—William E. Kamm
*Assistant Examiner*—Scott M. Getzow
*Attorney, Agent, or Firm*—Gottlieb, Rackman & Reisman

[57] ABSTRACT

An implantable, battery-operated cardioverting/defibrillating pacemaker device with the ability to sense and respond to haemodynamic compromise is described. The ventricular pressure (VP) and electrical activity of the heart are sensed via one or more transvenous or epicardial devices. The filtered peak-to-peak amplitude (VFPPA) and a peak pressure function (VPPF) based upon the right and/or left VP waveform(s) are derived. One of the VFPPA and VPPF, and electrically derived heart rate information, are used in the diagnosis of arrhythmic states. Bradycardia support pacing is initiated and terminated by reference to the VP signal, and the pacing pulse voltage used during bradycardia support pacing is optimized in order to extend battery life of the device. This is done by using the haemodynamic sensor to confirm the presence of an appropriate haemodynamic response to the delivery of bradycardia support pacing, and adjusting the pacing voltage to its lowest efficacious level. In the preferred embodiment the high pass filtered right ventricular pressure is monitored to confirm pacing capture.

28 Claims, 6 Drawing Sheets

FIG. 1.

| \multicolumn{4}{c}{TYPICAL RATE, RVPPF AND RVFPPA VALUES DURING ARRHYTHMIAS} |
| --- | --- | --- | --- |

| RATE | RVPPF | RVFPPA | THERAPY |
| --- | --- | --- | --- |
| <=120 | >60% | >80% | Normal pacing therapy |
| <=120 | <60% | <80% | Pacing Optimising algorithm |
| >120 | >50% | >50% | Antitachycardia pacing |
| >120 | >30% & <=50% | >30% & <=50% | Cardioversion |
| >120 | <=30% | <=30% | Defibrillation |

(Rate expressed as beats per minute. RVPPF and RVFPPA expressed as a percentage of resting values).

IMPLANTABLE AUTOMATIC AND HAEMODYNAMICALLY RESPONSIVE CARDIOVERTING/DEFIBRILLATING PACEMAKER WITH MEANS FOR MINIMIZING BRADYCARDIA SUPPORT PACING VOLTAGES

BACKGROUND OF INVENTION

This invention relates to an implantable cardioverting/defibrillating pacemaker and, more particularly, to a pacemaker of this type that is responsive to both an electrically derived heart rate and to a haemodynamic parameter.

An implantable haemodynamic cardioverting/defibrillating pacemaker is disclosed in United States patent application Ser. No. 481,364 to K. A. Collins, filed Feb. 16, 1990, and entitled "An Implantable Automatic and Haemodynamically Responsive Cardioverting/Defibrillating Pacemaker," which is assigned to the assignee of the present invention, and is incorporated herein by reference. The pacemaker of said application Ser. No. 481,364 overcomes many of the problems of false or inappropriate delivery of therapy that arise out of a reliance solely upon the sensing of the electrical activity of the heart as a means of determining the state of cardiac function.

Among the significant problems that face such an implantable device is the problem of increasing the device's battery life. Research has shown that bradycardia support pacing, in a cardioverting/defibrillating pacemaker, can consume between 10 and 30 percent of the total battery life of the device, depending on the pacing voltage used. Minimizing the battery consumption due to bradycardia support pacing will help reduce the risk of premature depletion of the battery of the device. At best, premature depletion forces the recipient of the device to undergo another general anesthetic. At worst, it may result in the death of the patient. Williams et al. in their article "Automatic Implantable Cardioverter-Defibrillator-Related Complications", J.A.C.C., Vol. 15 (2), Page 55A (1990), report that the death rate due to premature battery depletion in such devices was 0.6 percent.

It is well known that under different circumstances greater pacing energies are required. For example, after reversion of ventricular fibrillation, bradycardia support pacing often requires an increased pacing energy. One means of increasing pacing energies during a period of post reversion asystole is disclosed in the U.S. Pat. No. 4,869,252 of Norma L. Gilli, dated Sep. 26, 1989, which patent is assigned to the assignee of the present invention. In the disclosure of said Gilli patent, maximum pacing energies are provided regardless of the state of the heart. The Gilli patent also reveals a method for controlling pulse energy in antitachyarrhythmia and bradycardia support pacing. However, the Gilli patent is limited in that no means are provided for assuring that the capture of the heart is occurring, nor is any means provided therein for determining how low a pacing voltage can safely be used to ensure capture of the heart.

Mirowski et al., in U.S. Pat. Nos. 3,614,955 and 3,942,536, describe systems that sense heart function using the peak of the right ventricular pressure waveform. These devices suffer some obvious disadvantages including, among others, the fact that no haemodynamic parameters are provided to control the pacing voltage used during bradycardia support pacing.

A device disclosed in U.S. Pat. No. 4,774,950, to Cohen, has sought to overcome the shortcomings of common forms of cardioverting/defibrillating pacemakers by relying on the mean right ventricular pressure, mean arterial pressure, mean left atrial pressure, mean left ventricular pressure and/or mean central venous pressure as indicators of haemodynamic compromise. Background material relating to the Cohen invention can be found in an article by Cohen et al., entitled "Haemodynamic Responses to Rapid Pacing: A Model for Tachycardia Differentiation", PACE, Vol. 11, Pages 1522-1528 (1988). The Cohen device also is devoid of disclosure relating to the use of haemodynamic parameters to control the pacing voltage used during bradycardia support pacing.

As indicated earlier, one means of minimizing the energy consumed in bradycardia support pacing, and thereby extending the battery life of the pacemaker, is to reduce the pacing voltage used. In order to do this, the implantable device must have some means of determining whether or not the delivered pacing pulse has stimulated the heart to beat, i.e., determining whether or not the heart has been captured. In a haemodynamic cardioverting/defibrillating pacemaker, the signal from which the haemodynamic parameter is being derived can be used to determine whether or not the pacing pulse has captured the heart. A response to pacing, such as a pulsatile rise in the right ventricular pressure, can be used to confirm capture. The bradycardia support pacing voltage can thereafter be reduced until capture is lost, and then raised again to the lowest effective pacing voltage.

It is, therefore, a primary object of the present invention to provide an improved implantable, battery-operated device for the treatment of a malfunctioning heart that is capable of providing effective bradycardia support pacing at a lower mean energy level than has heretofore been the case in order to provide for increased battery life of the device.

Another object of the present invention is to provide an improved implantable, battery-operated device for the treatment of a malfunctioning heart, which device has sensing modalities for sensing both the heart's electrical function and its haemodynamic function, and which device utilizes sensed haemodynamic function information to enable it reduce the bradycardia support pacing voltage to the lowest effective level.

A further object of the present invention is to provide a two-sensing-modality, cardioverting/defibrillating pacemaking device in which the energy required for bradycardia support pacing can be minimized by sensing evoked ventricular pressure responses to bradycardia support pacing.

Additional objects of the invention include the provision of improved methods (i) for determining a patient's need for bradycardia support pacing; (ii) for optimizing bradycardia support pacing voltages delivered to a patient's heart; and, (iii) for terminating ongoing bradycardia support pacing of a patient's heart when the need for such pacing no longer exists.

Further objects and advantages of this invention will become apparent as the following description proceeds.

| SUMMARY OF TERMS | |
|---|---|
| ATP | Antitachycardia Pacing. |
| ECG | The ECG is, strictly speaking, a graphical representation of the electrical activity of the heart. However, the term ECG is used loosely to refer to the electrical activity of heart. The electrical activity of the heart can be sensed either on the surface of the skin, or on or in the heart. |
| L (Left) | Used to signify that an acronym refers to the left side of the heart as in: LVFPPA - Left Ventricular Filtered Peak-to-Peak Amplitude (VFPPA); LVP - Left Ventricular Pressure (VP); LVPPF - Left Ventricular Peak Pressure Function (VPPF); etc. |
| R (Right) | Used to signify that an acronym refers to the right side of the heart as in: RVFPPA Right Ventricular Filtered Peak-to-Peak Amplitude (VFPPA); RVP - Right Ventricular Pressure (VP); RVPPF - Right Ventricular Peak Pressure Function (VPPF); etc. |
| VF | Ventricular Fibrillation. |
| VFPPA | Ventricular Filtered Peak-to-Peak Amplitude. |
| VP | Ventricular Pressure. |
| VPPF | Ventricular Peak Pressure Function. |
| VT | Ventricular Tachycardia. |

TERMINOLOGY

A pacemaker is any device capable of electrically stimulating the heart to contract. Most such devices can also sense the electrical activity of a contracting heart and react to alterations in its electrical function. Most such devices are implanted and, if programmable, are interacted with via a telemetric link.

Rate Responsive or physiological pacemakers are pacemaking devices that are able to sense and respond to some indicator of increased tissue oxygen demand, for example respiratory rate. They respond by altering the paced heart rate to meet the changes in oxygen requirements.

A cardioverter/defibrillator is any device that can sense the presence of tachyarrhythmias and deliver an electric shock to a heart in order to revert it back to a normal rhythm. The difference between a cardioverter and a defibrillator lies only in the amount of energy delivered to the heart. Cardioversion is usually used to refer to low energy shocks, and defibrillation to high energy shocks. A cardioverter/defibrillator is usually capable of supplying energies in a range of less than one joule to more than forty joules. These shocks may or may not be synchronized with the R-wave of the ECG.

A cardioverting/defibrillating pacemaker is a device that can perform cardioverting, defibrillating and pacemaking functions. When referred to herein, it applies equally to devices that deliver their energy synchronously with a detected R-wave and to devices that do not. When used, the term will usually apply to devices that electrically sense and/or stimulate via electrodes in the right ventricle and atrium. However, it can also apply to devices that do so only in the right ventricle, in the right atrium alone, in multiple heart chambers via epicardial patches or leads, or via other sense/stimulation configurations.

Antitachycardia pacing (ATP) is a technique implemented in some pacemaking devices. Its aim is to pace a rapidly and abnormally beating heart back into a more normal rhythm. Its use implies that the tachyarrhythmia detected is considered not to be so sufficiently haemodynamically compromising that it will endanger vital organs within the anticipated treatment time. ATP may produce a more malignant tachyarrhythmia; for example, ventricular tachycardia (VT) may be paced into ventricular fibrillation (VF). For this reason ATP is normally implemented only when there is the option to use cardioversion/defibrillation therapy.

Wherever reference is made herein to a device that senses the right ventricular ECG (RVECG), and/or the right atrial ECG (RAECG), and the right ventricular pressure (RVP), the latter to derive the right ventricular FPPA (RVFPPA) and VPPF (RVPPF), and that uses this information to implement bradycardia pacing, antitachycardia pacing or defibrillation, it should be understood that the device can also sense and respond to the left ventricular ECG, and/or left atrial ECG, and left VP in a similar fashion, i.e., via deriving LVFPPA and LVPPF.

Capture is used to refer to the entrainment of the heart rhythm with pacing pulses. In this respect the evoked responses are the responses of the heart, once captured, to the pacing pulses delivered. There are many possible evoked responses: the main meaning being the electrophysiological response. In this disclosure the evoked response referred to is usually the initiation of ventricular contraction, as witnessed by the development of a pressure pulse within the ventricle.

SUMMARY OF THE INVENTION

Briefly stated, and in accordance with one embodiment of the invention, there is provided an implantable, battery-operated device for the treatment of a malfunctioning heart. The device includes a first sensing modality for sensing an electrical function in a patient's heart and providing a first signal representative of the electrical function, and a second sensing modality for sensing a haemodynamic function in the patient's heart and providing a second signal representative of the haemodynamic function. The device is also provided with a first means responsive to the first signal for analyzing the state of the heart's function and providing any required electrical shock pacing therapy to the heart at a initial predetermined energy level high enough to ensure prompt pacing capture of the heart. The device further includes a second means responsive to the second signal, and operative when evoked haemodynamic responses from the pacing therapy are sensed, to cause the energy level of the pacing therapy provided by the first means to be reduced from its initial predetermined level to a lower level, at which level pacing capture of the heart can be maintained and battery life of the device is increased relative to the battery life obtainable at the initial predetermined energy level.

In accordance with another embodiment, the invention provides a method of optimizing bradycardia support pacing voltages delivered to a patient's heart including the steps of (A) delivering a chain of bradycardia support pacing pulses at a predetermined voltage level to the heart; (B) monitoring the ventricular pressure waveform of the heart to assess whether or not pacing capture of the heart occurs during delivery of the chain of pulses; (C) if pacing capture of the heart occurs during step (B), decreasing the level of the bradycardia support pacing voltage delivered in step (A) to a minimum level, at which pacing capture is lost, and then raising the level of such voltage to an intermediate level, at which effective pacing capture is again achieved; and, (D) if pacing capture does not occur during steps (A) and (B), increasing the level of the bradycardia support pacing voltage delivered under step (A) until pacing capture of the heart occurs under step (B).

In accordance with yet another embodiment, the invention provides a method for determining the need for bradycardia support pacing of a patient's heart including the steps of (A) continuously monitoring a signal derived from a haemodynamic pressure waveform of the patient; (B) comparing the monitored signal with a predetermined threshold value; (C) detecting when the threshold value is crossed by the monitored signal to determine when heart contractions have occurred; and, (D) initiating bradycardia support pacing in the event a threshold crossing does not occur within a predetermined time period following the time at which a last-detected threshold crossing occurred, or within a predetermined time period following a last-detected heart contraction.

In accordance with a still further embodiment, the invention provides a method for determining the need for continuing ongoing bradycardia support pacing of a patient's heart including the steps of (A) continuously monitoring a signal derived from a haemodynamic pressure waveform of the patient during the application to the heart of bradycardia support pacing pulses; (B) comparing the monitored signal with a predetermined threshold value; (C) noting when the threshold value is crossed by the monitored signal to determine when heart contractions have occurred; and, (D) initiating a subsequent bradycardia support pacing pulse in the event a threshold crossing does not occur within a predetermined time period after a last-previous bradycardia support pacing pulse has been delivered.

In accordance with yet a further embodiment, the invention provides a method for terminating ongoing bradycardia support pacing of a patient's heart including the steps of (A) continuously monitoring both a first signal derived from a haemodynamic pressure waveform of the patient and a second signal representing electrical activity of the heart during the application to the heart of bradycardia support pacing pulses; (B) comparing the monitored first signal with a predetermined threshold value, and the monitored second signal with a predetermined QRS-wave complex; and, (C) terminating the bradycardia support pacing if, within a first predetermined time period after a last-previous bradycardia support pacing pulse has been delivered, either the first signal crosses the predetermined threshold value or the second signal displays QRS-wave pattern within the predetermined QRS-wave complex.

BRIEF DESCRIPTION OF THE DRAWINGS

While the specification concludes with claims particularly pointing out and distinctly claiming the subject matter of this invention, it is believed that the invention will be better understood from the following description, taken in conjunction with the accompanying drawings, in which:

DESCRIPTION OF THE PREFERRED EMBODIMENTS

Figure 2:
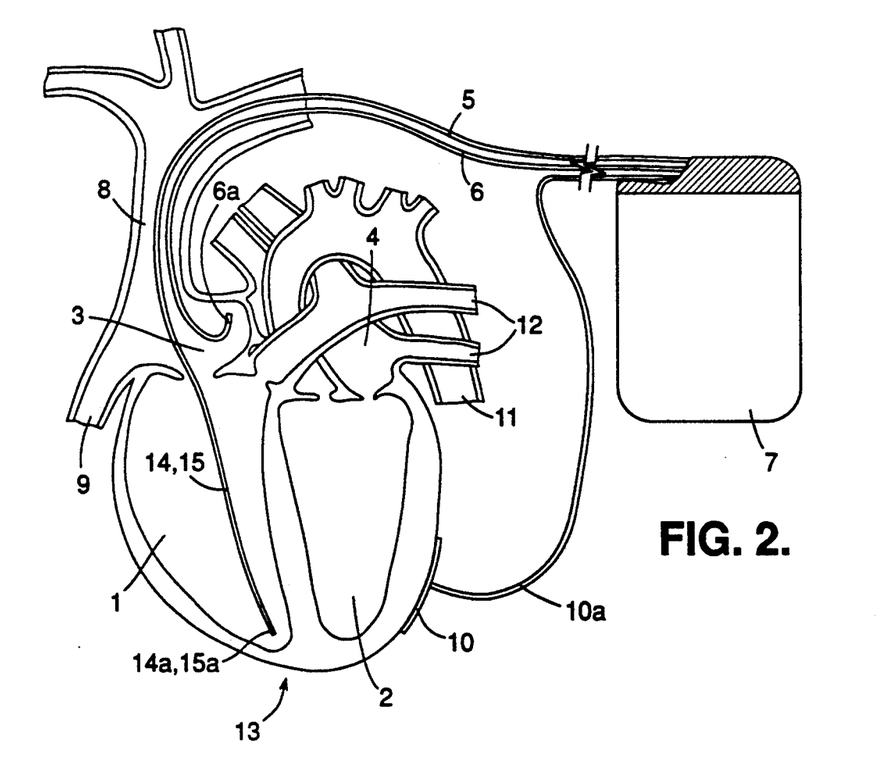
FIG. 2 is a schematic diagram of an implanted cardioverting/defibrillating pacemaker device in accordance with the present invention, positioned in the patient's body and showing electrical leads which interconnect the heart and the device.

Referring to FIG. 2, the invention is described herein in connection with its use in an implantable cardioverting/defibrillating pacemaker device, shown generally at 7, which is responsive both to an electrically derived heart rate and to a haemodynamic parameter, for example the device disclosed in the aforesaid Collins patent application Ser. No. 481,364. The device 7, which is preferably implemented as a dual chamber device but may also be implemented as a single chamber device, is permanently implanted in accordance with known practices at a point remote from the cardiac cavity, and is connected to the heart 13 by various leads. Thus, referring to FIGS. 2 and 3, a dual lead 5, which includes an ECG signal sensor lead 14 and a pressure sensor lead 15, interconnects an ECG signal sensor 14a and a pressure sensor 15a located in the right ventricle 1 of the patient's heart with the device 7. Similarly, one or more epicardial defibrillation patch(es), shown generally at 10, are connected to the device 7 by corresponding lead(s) 10a, and an atrial ECG signal sensor 6a is connected to the device 7 by an ECG lead 6. Other parts of the heart and its associated heart vessels include the left ventricle 2, the left atrium 4, the superior vena cava 8, the inferior vena cava 9, the aorta 11 and the pulmonary vessels 12.

Figure 3:
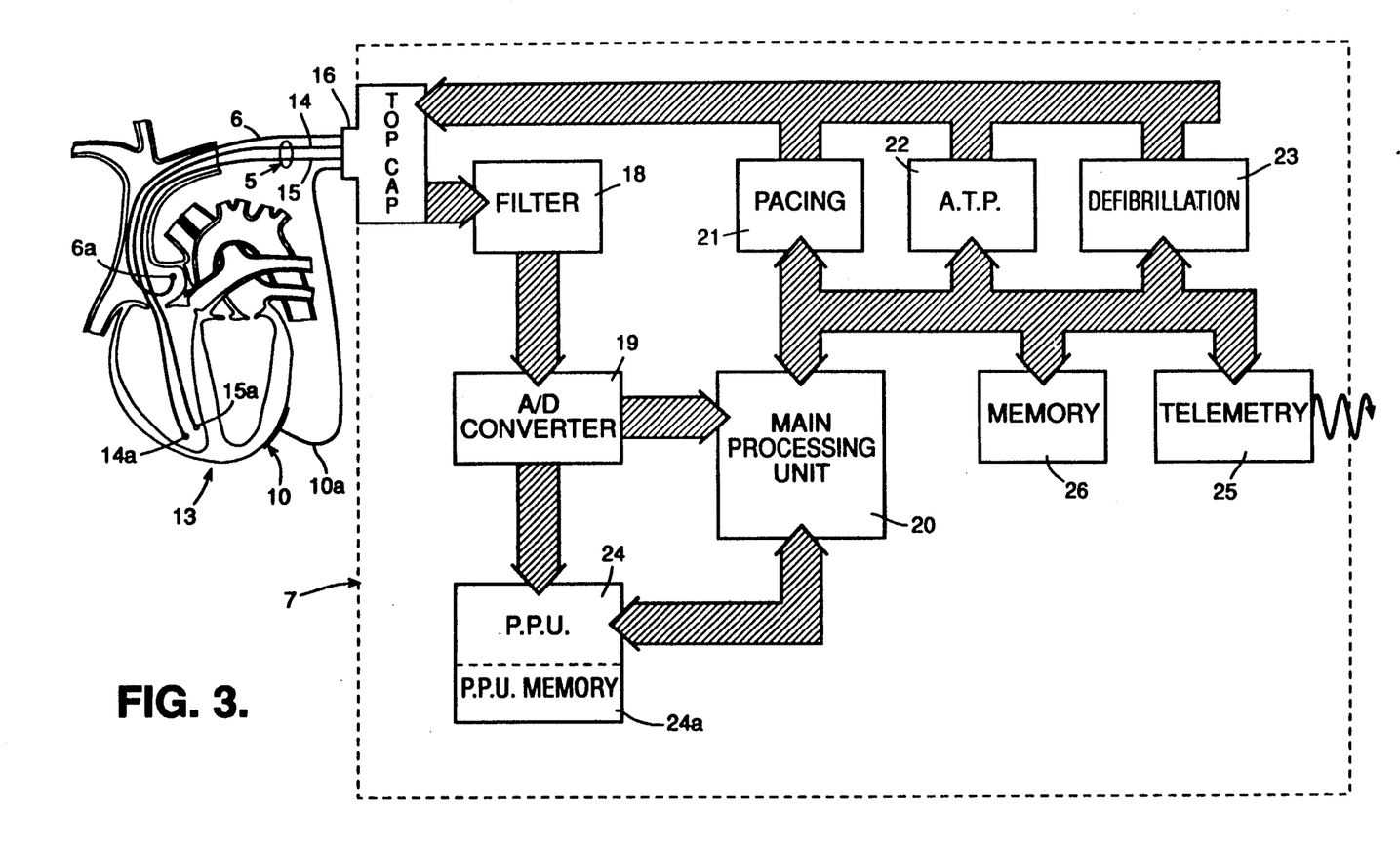
FIG. 3 is a block diagram of the device shown in FIG. 2, with blocks thereof representing either discrete components or logic units within one or more microprocessors of the device.

Referring more particularly to FIG. 3 the major circuits and logical units of the device have there been illustrated. In the preferred embodiment of this invention, the analog signals sensed by the various sensors in the heart are delivered by the leads 6, 10a, 14 and 15 through the top cap 16 of the device 7 to a high pass filter 18, wherein the VP waveform is filtered to remove its D.C. offset. The signals are then passed to an analogue-to-digital (A/D) converter 19 where they are converted to a digital format. The digital signals are then processed by the main processing unit (MPU) 20.

The main processing unit 20 controls the logic and circuitry of the bradycardia support pacing module 21, the antitachycardia pacing module 22 and the defibrillation module 23. The device 7 can be programmed by a telemetry link 25, and random access may be had to data storage registers or memory 26.

After being converted to digital form in A/D converter 19, data signals from the pressure sensing lead 15 are processed by a pressure processing unit (PPU) 24 that may be either a discrete circuit or a logical unit within the main processing unit 20. The pressure processing unit 24 is provided with a pressure processing unit memory 24a.

Figure 4:
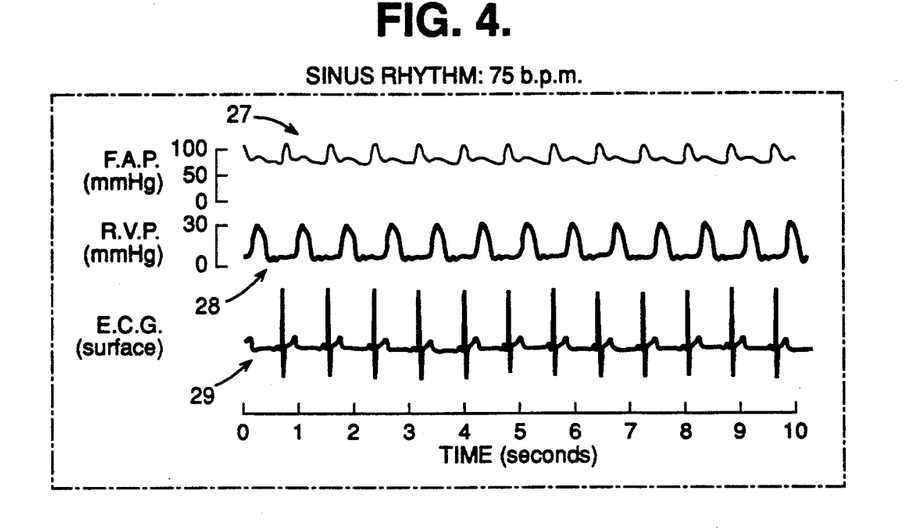
FIG. 4 is a representative diagram of normal femoral artery pressure, right ventricular pressure and ECG waveforms.

Referring now to FIG. 4, a typical RVP wave form is shown generally at 28, with the horizontal axis representing time in seconds, and the vertical axis representing the right ventricular pressure in millimeters of mercury. Similarly, a typical form of the pressure wave obtained in the femoral artery (FAP) is shown generally at 27, again with time being shown in seconds on the horizontal axis and the femoral artery pressure being shown in millimeters of mercury on the vertical axis. A surface ECG waveform is shown generally at 29, with time being shown on the horizontal scale and voltage being represented on the vertical scale. As may be seen by inspection of the various waveforms 27-29, the modulations of both pressure waveforms 27 and 28 fall between the R-waves of the ECG 29 during normal sinus rhythm at 75 bpm.

Figure 5:
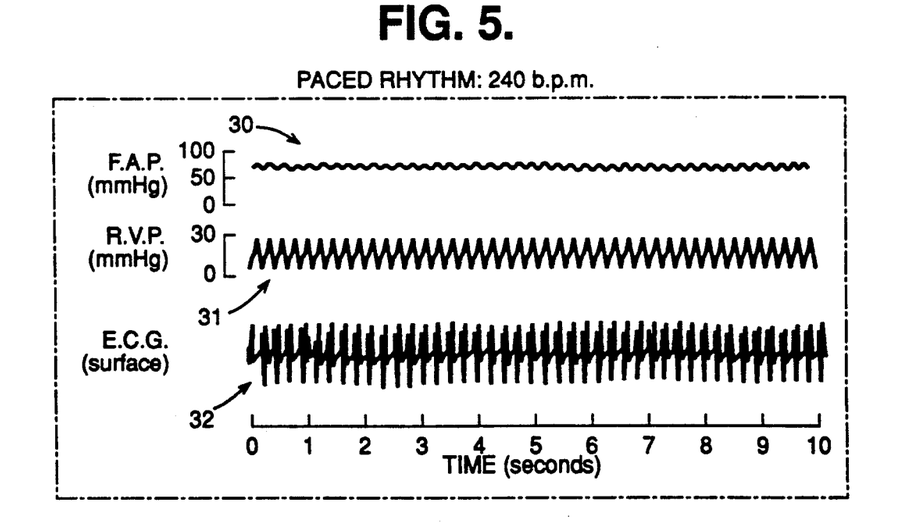
FIG. 5 is a representative diagram of femoral artery pressure, right ventricular pressure and ECG waveforms taken during ventricular pacing at 240 beats per minute (bpm)

Referring now to FIG. 5, the FAP waveform 30, the RVP waveform 31 and the ECG waveform 32 are shown with the corresponding heart beating at a paced rhythm of 240 bpm. As is apparent from an inspection of FIG. 5, the peak-to-peak amplitude of the RVP waveform 31 is well maintained even when the heart is paced to a high rate. It can also be seen that, at this rate, the FAP waveform is low but still life sustaining in the short term. It can also be seen that the peaks of the right ventricle and femoral artery waveforms both occur after the R-wave of the ECG.

Figure 6:
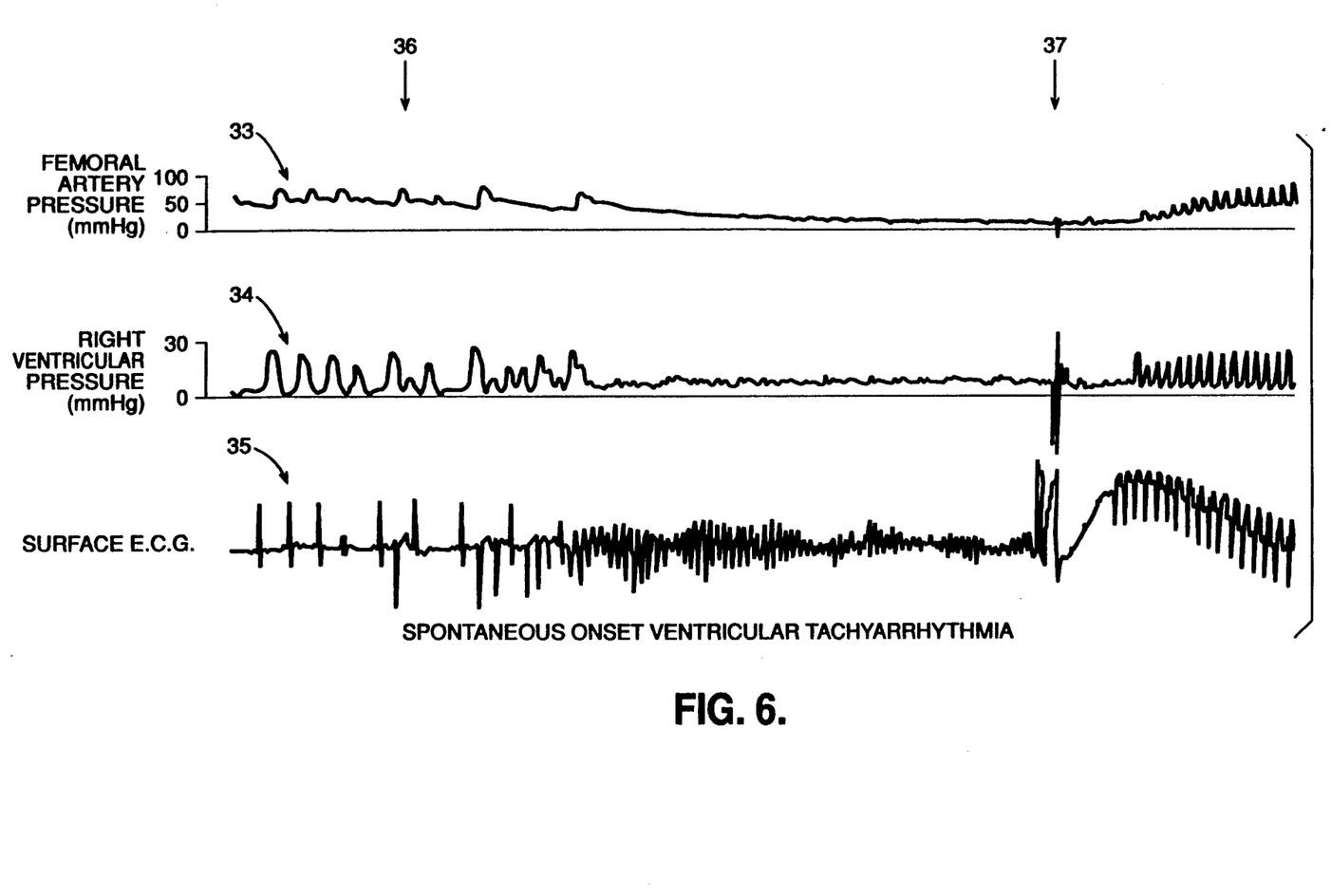
FIG. 6 is a representative diagram of femoral artery pressure, right ventricular pressure and ECG waveforms during an episode of ventricular fibrillation.

Referring now to FIG. 6, this figure depicts the typical changes in FAP waveform 33, RVP waveform 34 and ECG waveform 35 with the onset of ventricular fibrillation, shown at 36. It is noted that there is almost no modulation in either the RVP waveform 33 or the FAP waveform 34, and that the FAP is so low that life would cease unless action were taken. Normal function is returned after the administration of a defibrillating shock, shown at 37.

Referring back to FIG. 3, the pressure processing unit (PPU) 24 for the pressure waveform derives the right ventricular filtered peak-to-peak amplitude (RVFPPA) and the right ventricular peak pressure function (RVPPF) from the filtered and digitized right ventricular pressure (RVP) waveform. The PPU 24 communicates the derived data to the main processing unit (MPU) 20. The MPU 20 has access to the data registers (memory) 24a of the PPU 24.

The RVFPPA is obtained by filtering the RVP waveform with a high-pass filter having a 3 db frequency in the range of 0.1 to 0.5 Hz. In the preferred embodiments of the invention this filter is a second order Butterworth filter. The RVFPPA is derived from the filtered RVP waveform by determining the maximum excursion of the filtered signal over a defined time period. In the preferred embodiment this time period is determined by the period between R waves in the intracardiac ECG. The RVPPF is obtained by rectifying the filtered RVP waveform and then integrating it. The integral for each contraction is obtained by reference to the R-wave interval from the endocardial ECG. In the preferred embodiments of this device both the ECG signal and one or the other of the signals derived from the RVP waveform are used to determine whether or not the recipient of the device is haemodynamically comprised.

The device has two main implementations, each of which can be implemented using one of two algorithms. In the first algorithm (hereinafter referred to as the "simple threshold algorithm") the RVFPPA is monitored and compared to a threshold value. This value can be programmed as either an absolute value or as a percentage of a long term mean of the RVFPPA.

The threshold detector is linked to a simple counter (not shown). Each time the value of the RVFPPA becomes greater than the threshold value, the counter is reset to zero. This counter increments each time the RVFPPA is sensed and found to be lower than the threshold value. If this counter reaches a pre-programmed value, then haemodynamic comprise is deemed to exist. In the normally functioning recipient of this device, the rising edge of the RVFPPA would periodically reset the counter before the triggering value were reached. When the counter reaches the triggering level, the PPU 24 communicates this to the MPU 20, indicating that a state of haemodynamic compromise exists.

In the second algorithm (hereinafter referred as the "X out of Y algorithm"), the RVFPPA is assessed with each heart beat cycle as the sum of the greatest negative and positive digital values obtained over one cycle. The value is manipulated as a percentage of a programmed reference value and the values for the last "Y" beats are stored in memory, where "Y" is a programmed value. The RVPPF value is also calculated as a percentage of a programmed value and the values thereof for the last "Y" beats are also stored in memory.

If "X" out of the last "Y" beats, where "X" and "Y" are programmed values, fail to produce RVFPPA and/or RVPPF values above programmed levels, then the PPU 24 communicates this to the MPU 20, indicating that a state of haemodynamic compromise exists.

It is noted that for both detection algorithms the presence of a bradycardia is defined in terms of an electrically sensed bradycardia, with or without the pressure sensor detecting haemodynamic compromise. Asystole is defined in terms of the absence of electrical activity and of modulation in the RVFPPA.

The invention can be implemented in either of two embodiments, using either of the above algorithms. In the first embodiment of the device VFPPA and VPPF are continuously derived. In the second embodiment, the haemodynamic sensor is activated only when an electrical abnormality in the function of the heart is detected.

In the first embodiment the MPU 20 continuously monitors PPU 24, as well as the electrical activity of the heart. The result generated by the haemodynamic compromise detection algorithm is used in conjunction with information gained electrically about the heart rate to determine what therapy to initiate. Since both electrical and haemodynamic function of the heart are being continuously sensed, an abnormality in the function of either can initiate therapy. The use of different sensitivities to detect different conditions in electrically derived signals is described in the copending United States patent application Ser. No. 187,797 of R. Grevis and N. Gilli, filed Apr. 29, 1988, and entitled "Apparatus and Method for Controlling Multiple Sensitivities in Arrhythmia Control System Including Post-Therapy Pacing Delay," which is assigned to the assignee of the present invention and is also incorporated herein by reference.

Figure 1:
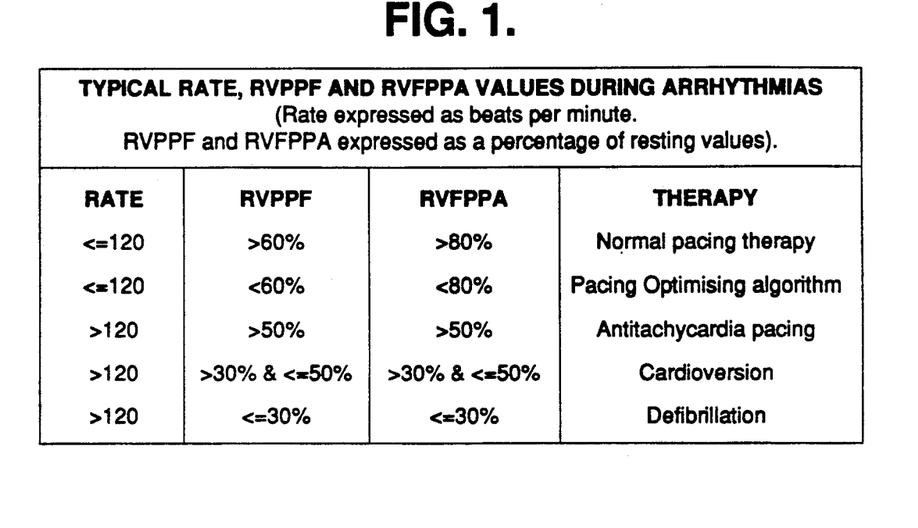
FIG. 1 is a table of representative RVFPPA and RVPPF values.

When a tachyarrhythmia is detected in accordance with the first embodiment of the present invention, therapy is initiated in accordance with the chart set forth in FIG. 1. It is noted that the chart of FIG. 1 is based on the use of a heart rate of 120 bpm as the dividing point between a tachyarrhythmia condition requiring electrical shock therapy and a condition not requiring antitachyarrhythmia electrical shock therapy. This value is a programmable initialization variable that would be set by the user/clinician based on his knowledge of and experience with the patient. It should also be pointed out that the use of a dual chambered configuration allows a lower energy cardioversion shock to be used to revert an atrial fibrillation that is haemodynamically compromising. This arrhythmia is recognized by the presence of an atrial rate that is higher than the ventricular rate, in the presence of haemodynamic compromise.

In the second embodiment of this device the MPU 20 will activate the PPU 24 to derive one of the RVFPPA and RVPPF values and initiate the programmed pressure sensing algorithm, as above, in the event that the device senses an electrical disturbance of the heart. It will then initiate therapy in accordance with the chart of FIG. 1. No therapy will be initiated if there is no evidence of haemodynamic compromise. The MPU 20 also periodically activates the PPU 24 to ensure that the FPPA and VPPF are within optimal normal limits. If they are not, then the MPU 20 will initiate its pacing optimization algorithm.

In both embodiments bradycardia support pacing is available and, during such support pacing, the device can be programmed to manipulate the bradycardia support pacing voltage. The logic behind the bradycardia support pacing voltage control algorithm is shown in block diagram form in FIG. 7. This algorithm is designed to function with existing technologies and, in particular with existing bradycardia support pacing, antitachycardia pacing and cardioverting/defibrillating therapies. In the preferred embodiment of the invention, the algorithm is executed from software resident within the microprocessor of device 7. Alternatively, it may be implemented as discrete digital circuitry.

In the first embodiment of device 7, wherein haemodynamic pressure is monitored continuously, bradycardia support pacing is initiated if the device fails to detect either a QRS-wave event or a pressure pulse event within a given time period after the last sensed event. The sensing of a QRS-wave event is done in accordance with known technologies (e.g., the technology disclosed by Baker, Jr. et al., in U.S. Pat. No. 4,280,502, entitled "Tachycardia Arrester". The sensing of a pressure pulse may be done by comparing the high-pass filtered right ventricular pressure (RVP) waveform with a pre-programmed threshold level that is typically equal to the ventricular fibrillation (VF) detection threshold.

A diagnosis of asystole requires that the device look for but not find a crossing of a threshold pressure value within a pre-programmed time period after either the last pressure pulse detection was made or after the last-sensed QRS wave. The length of the aforesaid time period is controlled by a variable that can be programmed by the attending physician.

Figure 7:
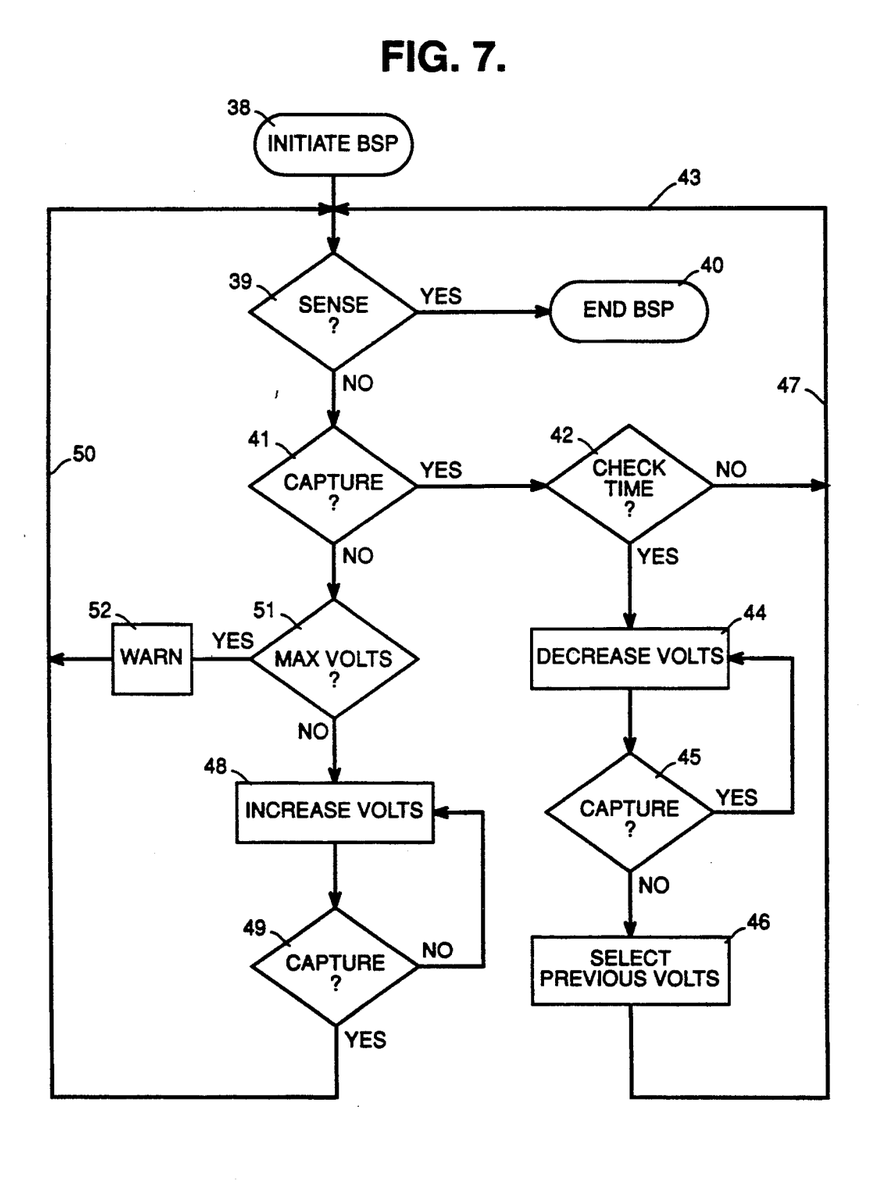
FIG. 7 is a logic flow diagram of a program that may be utilized for minimizing bradycardia support pacing voltages; and, FIG. 8 is a logic flow diagram of a program that may be utilized for determining whether or not pacing capture of the heart has occurred.

Referring to FIG. 7, this is a logic flow chart for the algorithm that controls the pacing voltage during bradycardia support pacing in an inhibited mode, as is used in the preferred embodiment of the device. In the case of inhibited bradycardia support pacing, as shown at 38, the detection of a spontaneous QRS wave and/or a pressure threshold crossing, as shown at 39, inhibits the bradycardia support pacing, as indicated at 40. Otherwise, bradycardia support pacing is initiated at the rate programmed by the attending physician.

The voltage used for this pacing will be the programmed pacing voltage if this is the first time that bradycardia support pacing has been initiated since the device was last programmed. Otherwise the initial voltage will be the last optimal voltage obtained during the previous episode of bradycardia support pacing.

The haemodynamic pressure response to the delivery of bradycardia support pacing is monitored, as shown at 41, in connection with determining whether or not pacing capture of the heart has occurred. This can be done by one of several methods, as discussed below. At regular intervals 42 throughout bradycardia support pacing, the pacing voltage is minimized by reducing it to the minimal level required to gain capture. The aforesaid interval is determined by reference to a programmed variable accessible to the attending physician. At times other than this programmed interval, provided capture of the heart is maintained, bradycardia support pacing continues uninterrupted, as indicated by the return-loop line 43.

At the aforesaid intervals, the pacing voltage is adjusted to its lowest functional level by decreasing it in a step-wise fashion, as indicated at 44, until capture is lost, as shown at 45. The size of the step is a variable that can be programmed by the attending physician but is typically 0.5 volts. The pacing voltage is then set to the lowest voltage that was able to sustain capture of the heart, as shown at 46. After the optimal pacing voltage has been found, the system returns to standard bradycardia support pacing, as shown at 47. The pacing voltage is not again adjusted until the aforesaid interval again elapses or unless capture of the heart during bradycardia support pacing is lost.

If at any stage a proper haemodynamic pressure response to a delivered bradycardia support pacing pulse is not detected at 41, then the pacing voltage is increased, as shown at 48, in step-wise increments until a pressure response is detected, as shown at 49. The size of the step is a variable that can be programmed by the attending physician but is typically 0.5 volts. Bradycardia support pacing is then resumed at this pacing voltage, as indicated by the return loop 50. If the pacing voltage is ever increased to its maximum value, as indicated at 51, then the device can be programmed to provide the patient with a tactile warning and to inform the attending physician that this has occurred upon the next time that the telemetry link is established, as shown at 52.

As indicated earlier, pacing capture, denoted at 41, can be determined by one of two methods. In the first method, a pacing pulse is delivered and the high-pass-filtered right ventricular pressure is monitored for a programmed interval after the delivery of the pacing pulse. If the pressure value crosses a programmed threshold during the programmed interval, then capture is deemed to have occurred.

Figure 8:
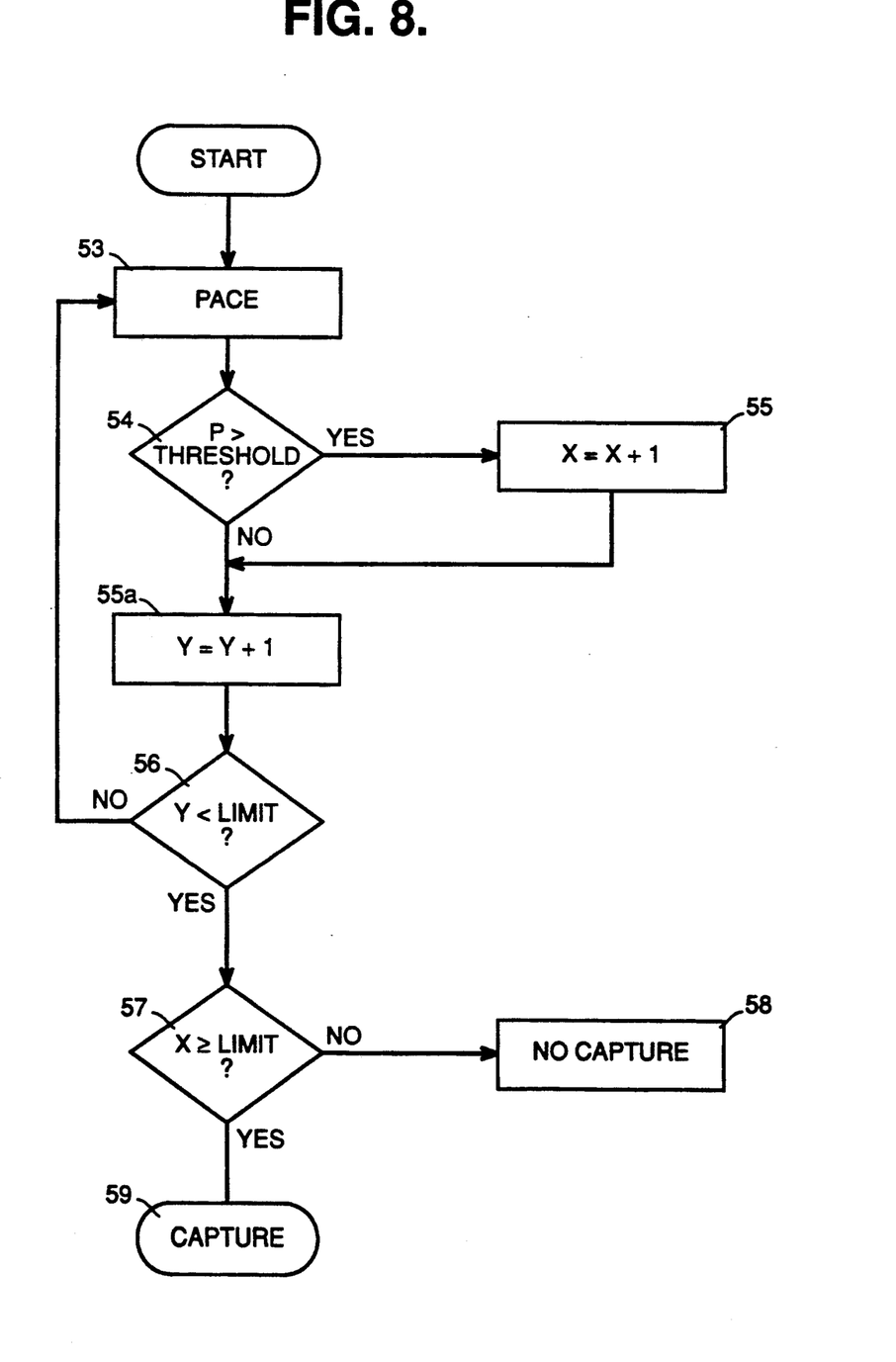

A second method for determining that pacing capture has occurred is shown in FIG. 8. In this method, bradycardia support pacing pulses are delivered at a pre-programmed interval, as indicated at 53. A pressure response is searched for during a programmed interval after each pace, as shown in 54, and the number of crossings of a programmed threshold is counted, as shown at 55. Typically, the ventricular fibrillation detection threshold is the minimum pressure response that is sought but other values may be programmed. After a predetermined number (e.g., "Y") of pacing pulses, which are counted at 55a, have been delivered, as indicated at 56, and if a second predetermined number (e.g., "X") or more pressure detections occur in response to the delivered "Y" pacing pulses, as shown at 57, then capture is deemed to have occurred, as indicated at 59. If less than "X" pressure detections occur in response to "Y" pacing pulses, then capture is deemed not to have occurred, as indicated at 58.

Regardless of the method used to determine capture, if at any time a pressure pulse and/or a QRS wave is detected before a programmed time has passed, then a spontaneous contraction is deemed to have occurred. In this event, bradycardia support pacing is discontinued if the device is operating in an inhibited mode.

In the preferred embodiment of the invention, the device 7 is implemented to have VVI pacing (inhibited ventricular pacing and sensing). However, the device can be embodied to permit all standard pacing formats for dual and single channel pacing. In the event of dual channel pacing (i.e., both atrium and ventricle being paced) then a pressure sensor is required for both the atrium and the ventricle if the atrial pacing voltage is to be controlled.

In the preferred embodiment of the invention, maximum use is made of software control of the device. However, as indicated earlier, the device can be implemented using discrete circuitry, rather than software.

It will be apparent from the foregoing description that this invention provides an improved implantable, battery-operated device for the treatment of a malfunctioning heart that is capable of providing effective bradycardia support pacing at a lower mean energy level then has heretofore been the case in order to provide for increased battery life of the device. Moreover, the present invention provides such a pacemaker device having two sensing modalities for sensing both the heart's electrical function and its' haemodynamic function, and which utilizes sensed haemodynamic function information to enable it to reduce the bradycardia support pacing voltage to the lowest effective level. Also, the invention provides a two-sensing modality, cardioverting/defibrillating pacemaking device in which the energy required for bradycardia support pacing can be minimized by sensing evoked ventricular pressure responses to bradycardia support pacing. Similarly, improved methods are provided by the present invention (i) for determining a patient's need for bradycardia support pacing; (ii) for optimizing bradycardia support pacing voltages delivered to a patient's heart; and, (iii) for terminating ongoing bradycardia support pacing of a patient's heart when the need for such pacing no longer exists.

While particular embodiments of this invention have been shown and described, it will be obvious to those skilled in the art that various other changes and modifications may be made without departing from the invention in its broader aspects, and it is, therefore, aimed in the appended claims to cover all such changes and modifications as fall within the true spirit and scope of this invention.

What is claimed is:

1. An implantable, battery-operated device for the treatment of a malfunctioning heart, said device including a first sensing modality for sensing an electrical function of a patient's heart and providing a first signal representative of said electrical function, a second sensing modality for sensing an haemodynamic function of the patient's heart and providing a second signal representative of said haemodynamic function, first means responsive to said first signal for analyzing the state of the heart's function and providing any required electrical shock pacing therapy to the heart at an initial predetermined energy level high enough to ensure prompt pacing capture of the heart, and second means responsive to said second signal and operative when evoked haemodynamic responses from said pacing therapy are sensed to cause the energy level of said pacing therapy provided by said first means to be reduced from said initial predetermined level to a lower level, at which pacing capture of the heart can be maintained and battery life of the device is increased relative to the battery life obtainable at said predetermined energy level.

2. A device according to claim 1, wherein said second signal comprises the filtered peak-to-peak amplitude of a ventricular pressure waveform of the heart.

3. A device according to claim 2, wherein said second signal comprises the filtered and rectified integration of a ventricular pressure waveform of the heart.

4. A device according to any one of claims 1-3, wherein said ventricular pressure waveform of the heart is the right ventricular pressure waveform of the heart.

5. A device according to any one of claims 1-3, wherein said device comprises a dual chamber, cardioverting/defibrillating pacemaker.

6. An implantable, programmable, battery-operated device for sensing malfunctions in a patient's heart and initiating therapy therefor based on the heart's electrical and haemodynamic functions, comprising:
   first means for calculating both the filtered and rectified integration of the pressure waveform of the right ventricle of the heart and the filtered peak-to-peak amplitude of such pressure waveform;
   second means for determining haemodynamic compromise based upon at least one of said calculations of said first means;
   third means for initiating appropriate electrical therapy for the heart based on the determination by said second means that haemodynamic compromise exists; and,
   fourth means operative following initiation of bradycardia support pacing therapy at a predetermined voltage level, and based on a sensing of the presence of bradycardia-support-pacing-evoked-responses in the right ventricular pressure, for lowering the level of the voltage utilized in said bradycardia support pacing to prolong the battery life of the device.

7. A device according to claim 6, wherein said fourth means progressively reduces said bradycardia support pacing voltage level until pacing capture of the heart is lost, and then progressively increases said voltage level until pacing recapture of the heart occurs.

8. A device according to any one of claims 6 or 7, wherein said device comprises a dual chamber cardioverting/defibrillating pacemaker.

9. A method of optimizing bradycardia support pacing voltages delivered to a patient's heart, comprising the steps of:
   (A) Delivering a chain of bradycardia support pacing pulses at a predetermined voltage level to the heart;

(B) Monitoring the ventricular pressure waveform of the heart to assess whether or not pacing capture of the heart occurs during delivery of said chain of pulses;

(C) If pacing capture of the heart occurs during step (B), decreasing the level of the bradycardia support pacing voltage delivered in step (A) to a minimum level at which pacing capture is lost, and then raising the level of said voltage to an intermediate level at which effective pacing capture is again achieved; and, (D) If pacing capture does not occur during steps (A) and (B), increasing the level of the bradycardia support pacing voltage delivered under step (A) until pacing capture of the heart occurs under step (B).

10. A method according to claim 9, including the further step of:

(E) providing a warning signal in the event that the level of the bradycardia support pacing voltage delivered during step (D) reaches a predetermined maximum level.

11. A method according to claim 9, wherein the voltage level decrease of step (C) and the voltage level increases of steps (C) and (D) are incremental and progressive.

12. A method according to claim 11, wherein the ventricular pressure waveform monitored in step (B) is the right ventricular pressure waveform.

13. A method according to claim 12, wherein the right ventricular pressure waveform is monitored during step (B), and wherein a filtered peak-to-peak amplitude is derived from said right ventricular pressure waveform to assess whether or not pacing capture of the heart occurs during step (B).

14. A method according to claim 13, including the further step of:

(E) providing a warning signal in the event that the level of the bradycardia support pacing voltage delivered during step (D) reaches a predetermined maximum level.

15. A method of determining whether or not pacing capture of a heart occurs during the application of bradycardia support pacing therapy to the heat, comprising the steps of providing bradycardia support pacing to the heart; monitoring the ventricular pressure waveform response for a programmed predetermined time period after a bradycardia support pacing pulse has been delivered to the heart; and, deeming pacing capture to have occurred in the event that the pressure waveform crosses a threshold value within said predetermined time.

16. A method of determining whether or not pacing capture of a heart occurs during the application of support pacing therapy to the heart, comprising the steps of pacing the heart and monitoring the ventricular pressure waveform response for a programmed predetermined time period after a pacing pulse has been delivered to the heart; and, deeming pacing capture to have occurred in the event that the pressure waveform crosses a threshold value a predetermined number of times in response to an equal or a predetermined larger number of pacing pulses.

17. A method according to any one of claims 15 or 16, wherein the right ventricular pressure waveform of the heart is passed through a high-pass filter and digitized to provide a derived right ventricular peak-to-peak amplitude signal which is monitored for said programmed predetermined time to determine whether or not said threshold value has been crossed.

18. A method for determining the need for bradycardia support pacing of a patient's heart, comprising the steps of:

(A) continuously monitoring a signal derived from a haemodynamic pressure waveform of the patient;

(B) comparing said monitored signal with a predetermined threshold value;

(C) detecting when said threshold value is crossed by said monitored signal to determine when heart contractions have occurred; and, (D) initiating bradycardia support pacing in the event a heart contraction does not occur within a predetermined time period following a last-detected heart contraction.

19. A method for determining the need for bradycardia support pacing of a patient's heart, comprising the steps of:

(A) continuously monitoring a signal derived from a haemodynamic pressure waveform of the heart;

(B) comparing said monitored signal with a predetermined threshold value;

(C) detecting when said threshold value is crossed by said monitored signal to determine when heart contractions have occurred; and, (D) initiating bradycardia support pacing in the event a threshold crossing does not occur within a predetermined time period following the time at which the last-detected threshold crossing occurred.

20. A method for determining the need for continuing ongoing bradycardia support pacing of a patient's heart, comprising the steps of:

(A) continuously monitoring a signal derived from a haemodynamic pressure waveform of the patient during the application to the heart of bradycardia support pacing pulses;

(B) comparing said monitored signal with a predetermined threshold value;

(C) noting when said threshold value is crossed by said monitored signal to determine when heart contractions have occurred and;

(D) initiating a subsequent bradycardia support pacing pulse in the event a threshold crossing does not occur within a predetermined time period after a last-previous bradycardia support pacing pulse has been delivered.

21. A method according to any one of claims 18-20, wherein said signal is derived from a ventricular pressure waveform of the heart.

22. A method according to claim 21, wherein said signal comprises a high-pass-filtered, digitized representation of the right ventricular pressure waveform of the heart.

23. A method according to claim 21, wherein said signal comprises a rectified, integration of a high-pass-filtered, digitized representation of the right ventricular pressure waveform of the heart.

24. A method for terminating ongoing bradycardia support pacing of a patient's heart, comprising the steps:

(A) continuously monitoring both a first signal derived from a haemodynamic pressure waveform of the patient and a second signal representing electrical activity of the heart during the application to the heart of bradycardia support pacing pulses;

(B) comparing said monitored first signal with a predetermined threshold value and said monitored second signal with a predetermined QRS-wave complex; and, (C) terminating said bradycardia support pacing if, within a first predetermined time after a last-previous bradycardia support pacing pulse has been delivered, either said first signal crosses a predetermined threshold value or said second signal displays a QRS-wave pattern within said predetermined QRS-wave complex.

25. A method according to claim 24, wherein said first signal is derived from a ventricular pressure waveform of the heart.

26. A method according to claim 25, wherein said first signal comprises a high-pass-filtered, digitized representation of the right ventricula pressure waveform of the heart.

27. A method according to claim 25, wherein said first signal comprises a rectified, integration of a high-pass-filtered, digitized representation of the right ventricular pressure waveform of the heart, and said second signal comprises an ECG waveform of the heart.

28. A method according to any one of claims 24–27, wherein pacing capture of the heart is determined during a programmed second predetermined time period after a bradycardia support pacing pulse has been delivered, and wherein said first predetermined time period elapses before the start of said second predetermined time period.

* * * * *